United States Patent [19]

Whittlinger

[11] Patent Number: 4,622,168
[45] Date of Patent: Nov. 11, 1986

[54] STABILIZER FOR AMINE/QUATERNARY AMMONIUM BLENDS

[75] Inventor: David E. Whittlinger, Janesville, Wis.

[73] Assignee: Sherex Chemical Company, Inc., Dublin, Ohio

[21] Appl. No.: 725,253

[22] Filed: Apr. 19, 1985

[51] Int. Cl.$^4$ .................. B01F 17/16; B01F 17/18; B01F 17/32
[52] U.S. Cl. .................. 252/352; 252/8.75; 252/8.8; 252/311.5; 252/315.2; 252/355; 252/357
[58] Field of Search .............. 252/352, 355, 357, 542, 252/8.75, 8.8

[56] References Cited

U.S. PATENT DOCUMENTS

| | | | |
|---|---|---|---|
| 3,681,241 | 8/1972 | Rudy | 252/542 X |
| 4,181,632 | 1/1980 | Schebece | 252/542 |
| 4,230,590 | 10/1980 | Wixon | 252/542 X |
| 4,448,916 | 5/1984 | Martenson | 252/8.75 X |

FOREIGN PATENT DOCUMENTS 0076572 4/1983 European Pat. Off. .......... 252/8.75

*Primary Examiner*—Richard D. Lovering
*Attorney, Agent, or Firm*—Mueller and Smith

[57] ABSTRACT

Disclosed is a method for improving the storage stability of a blend of an amine and an imidazolinium compound. Such method comprises adding an effective amount of a bisulfite agent to said blend. The stabilized blend is especially stable at elevated temperatures of storage.

15 Claims, No Drawings

STABILIZER FOR AMINE/QUATERNARY AMMONIUM BLENDS

BACKGROUND OF THE INVENTION

The present invention relates to the preparation of quaternary ammonium blends and more particularly to the stabilization of such blends.

Quaternary ammonium compounds have found wide acceptance in the marketplace for formulating fabric softeners and anti-stats, floculating agents, emulsifiers (e.g. for asphalt), personal care additives, clay/amine complexes, and the like. Some quaternary ammonium compounds can be unstable under extended storage conditions resulting in phase separation of the product. This same stability problem also can be encountered when dealing with some of the tertiary amine precursor of the quaternary ammonium compound. For some purposes, it is desirable to have the ability to transport and store the amine/quaternary ammonium blend for use as is or converting the amine portion of the blend into a quaternary ammonium compound, especially when end use of the blend is at a manufacturing location quite distant from the manufacturing source of the blend. An example of such instance would involve the manufacture of the amine precursor in one country for shipment to another country located a great distance therefrom. Under such circumstances, the end use country may desire the precursor amine to provide it the flexibility in converting the tertiary amine to different quaternary ammonium compounds, to use the amine precursor as is, or to blend it with other ingredients. Having the ability only to ship the quaternary ammonium product lessens the flexibility were the amine precursor to be able to be shipped and stored.

A practical problem in the extended storage and transport of such materials involves the conditions to which such materials will be subjected. For example, the product may be shipped in a ship cargo hold which may subject the product to high temperatures of storage, especially if the ship were sailing in equatorial waters. In order to provide requisite storage stability to such amine precursor or quaternary ammonium compounds during extended storage and shipment at elevated temperatures, a stabilizing agent or stabilizer often is added. Unfortunately, stabilizers which are suitable for either the precursor amine or for the quaternary ammonium compound often are undesirable for stabilizing blends of a quaternary ammonium compound and amine precursor.

BROAD STATEMENT OF THE INVENTION

The present invention addresses the storage stability of a blend of an amine and an imidazolinium compound, especially when the blend is subjected to elevated temperatures of storage. The method for improving the storage stability of such blend in accordance with the present invention comprises adding an effective amount of a bisulfite agent to the blend. Another aspect of the present invention is the resulting storage stabilized blend which comprises an amine, an imidazolinium compound, and an effective amount of a bisulfite agent.

Advantages of the present invention include the ability to at least retain, if not improve, the color of the amine/imidazolinium blend under extended storage conditions. Another advantage is that the stabilized blend of the present invention expresses improved stability at elevated temperatures of storage compared to room temperature storage of the stabilized blend. A further advantage is that the amine/imidazolinium blend can be subjected to full quaternization to provide a quaternary ammonium softener blend equivalent in properties and performance to an equivalently manufactured composition wherein full quaternization is accomplished prior to any storage conditions. These and other advantages will be readily apparent to those skilled in the art based upon the disclosure contained herein.

DETAILED DESCRIPTION

The bleaching and stabilizing effect imparted by the bisulfite agents of the present invention appears to be more effective at elevated storage temperatures than at lower or room temperature storage temperatures. The reasons for such elevated temperature storage stability are not fully understood, though they can be used to advantage in providing the ability to expose amine/imidazolinium blends to more stringent storage conditions without adversely affecting the stability of such blend. This can translate into reduced storage costs by not being forced to moderate temperatures in a cargo hold, railroad boxcar, or other transportation means typically utilized in transporting the amine/imidazolinium blends. Concomitant with the stability enhancement achieved with the present invention is the retention of performance and physical properties of the blend as is or when fully quaternized to make products as described above.

As the Examples will demonstrate, imidazolinium quaternary ammonium compounds neat tend to respond to peroxide agents much better than to bisulphite agents with respect to bleaching and stabilizing of the imidazolinium compounds. Accordingly, when an amine was blended with an imidazolinium compound, it was expected that the same peroxide agents would be effective in stabilizing the thus-formed amine/imidazolinium blends. Unexpectedly, however, acceptable color of the product only was marginally attainable at room temperature storage of the blend. At elevated storage temperatures (e.g. above about 100°–110° F., the blend rapidly darkened to an unacceptable level. The addition of a bisulfite agent was determined to be effective at stabilizing the blend against color deterioration over extended periods of storage and was even more effective at elevated temperatures of storage.

The amine portion of the blend can be a primary amine, a secondary amine, a tertiary amine, including polyamines. Preferably, however, the amines will be tertiary amines so that quaternization of such tertiary amines upon termination of storage can be practiced. Since quaternization of the tertiary amines is advantageous, such tertiary amines will be precursors for forming quaternary ammonium softening compounds. Such tertiary amines can be, for example, soya dimethyl amine, hydrogenated tallow dimethyl amine, palmityl dimethyl amine, cocoa dimethyl amine, allyl dimethyl amine, benzyl dimethyl amine, dialkyl($C_{12}$–$C_{18}$)methyl amine, di(hydrogenated tallow)methyl amine, bis(2-hydroxy ethyl)cocoa amine, bis(polyhydroxy ethyl)alkyl amine, methyl alkyl(e.g. $C_{10}$–$C_{18}$)benzyl amine, and the like and mixtures thereof. As noted above, such tertiary amines can be quaternized for forming quaternary ammonium compounds useful as softeners, surfactants, and a wide variety of additional uses. The blend broadly will contain at least about 5 weight percent amine and such proportion of amine often can range up to about 50 percent or greater.

A wide variety of imidazolinium compounds may be used in forming the amine/imidazolinium compound blends of the present invention. As noted above, such imidazolinium quaternary compounds often are stabilized more effectively with peroxide agents than with bisulfite agents. Representative imidazolinium quaternary compounds suitable for use in forming the stabilized blends of the present invention include, for example, methyl-1-hydrogenated tallow amido ethyl-2-hydrogenated tallow imidazolinium methyl sulfate, methyl-1-tallow amido ethyl-2-tallow imidazolinium methyl sulfate, methyl-1-oleyl amido ethyl-2-oleyl imidazolinium methyl sulfate, 1-ethylene bis(2-tallow, 1-methyl, imidazolinium methyl sulfate), and the like and mixtures thereof. Such imidazolinium quaternary compounds find acceptability in the marketplace as fabric softeners and can be used for their surface active properties additionally.

Bisulfite agents can be formed from a variety of alkali metal (e.g. Li, Na, K, etc.) and alkaline earth metals (e.g. Mg, Ca, Ba, etc.) for use in forming the stabilized blend of the present invention. The preferred treating agent, however, is sodium bisulfite. The proportion of bisulfite treating agent will be an effective amount for the particular blend being stabilized. Such effective amount broadly will be greater than about 0.3 weight percent by weight of the blend and such proportion can range on up to 1 percent or greater. Proportions in excess of an effective amount, however, do not provide increased stability, yet increase manufacturing costs. The presence of the bisulfite agent will not interfere significantly with the quaternization of the blend nor in its properties and performance.

As noted above, the stabilized amine/imidazolinium blend can be subjected to full quaternization with an alkylating agent in conventional fashion. Suitable alkylating agents include, for example, alkyl sulfate, alkyl halide, alkyl acetate, alkyl formate, and the like and mixtures thereof. Suitable alkyl groups traditionally will be lower alkyl groups, e.g. $C_1-C_4$ alkyl groups, though higher alkyl groups may be used on occasion depending upon steric considerations of the tertiary amine molecule being quaternized.

The following examples show how the present invention has been practiced, but should not be construed as limiting. In this application, all percentages and proportions are by weight and all units are in the metric system, unless otherwise expressly indicated. Also, all citations referred to herein are expressly incorporated herein by reference.

EXAMPLES

EXAMPLE 1

Lots of methyl-1-hydrogenated tallow amide ethyl-2-hydrogenated tallow imidazolinium methyl sulfate (molecular weight of 605, percent free amine of 0.8%, pH (5% in 1:1 isopropanol/water) of 7.0) was stabilized with hydrogen peroxide or sodium bisulfite and subjected to stability evaluation at various storage temperatures, i.e. 21.11° C. (70° F.), 48.88° C. (120° F.), 60° C. (140° F.), and 71.11° C. (160° F.). The Control lot was 200 g. The peroxide stabilized lot was 500 g. imidazolinium compound pH adjusted to 8.8 with 2 g. of 25% sodium methylate after adding 0.2 g. of trisodium hydroxy ethyl ethylene diamine triacetic acid chelating agent, 0.2 g of amino-tri(methylene phosphonic acid)penta-sodium salt chelating agent, and 5.3 g. of 50% aqueous hydrogen peroxide. The peroxide was permitted to react for one hour (pH 8.4). Thereafter, the pH was readjusted to 6.6 by the addition of about 1.5 g. of 10% HCl. The final peroxide content as 280 meq./kilogram. The bisulfite stabilized lot was 500 g. imidazolinium compound to which had been added 5 g. of 33% active aqueous sodium bisulfite solution followed by stirring for one-half hour. The following stability results were recorded.

TABLE 1

| Storage Time (Days) | Color Stability (Hellige Color 1933) Storage Temperature (°C.) | | | |
|---|---|---|---|---|
| | 21.11 | 48.88 | 60.00 | 71.11 |
| Control | | | | |
| Initial | 9+ | 9+ | 9+ | 9+ |
| 3 | 12− | 12+ | 13+ | 14+ |
| 7 | 12 | 12+ | 14+ | 14+ |
| 11 | 12 | 12+ | 14 | 15− |
| 21 | 12− | 12+ | 14− | 15+ |
| Bisulfite Stabilized Lot | | | | |
| Initial | 10+ | 10+ | 10+ | 10+ |
| 3 | 10− | 9+ | 9 | 10− |
| 7 | 8+ | 8+ | 8+ | 10+ |
| 11 | 8+ | 8+ | 8+ | 11− |
| 21 | 9− | 9− | 9− | 11− |
| Peroxide Stabilized Lot | | | | |
| Initial | 6− | 6− | 6− | 6− |
| 3 | 6+ | 6− | 6 | 6 |
| 7 | 6− | 6− | 6+ | 6 |
| 11 | 6− | 5+ | 6+ | 6+ |
| 21 | 6− | 6− | 6+ | 7+ |

The above-tabulated results clearly demonstrate the superiority of peroxide in stabilizing an imidazolinium quat compared to bisulfite. Based on these results, it would be expected that peroxide also would be more effective in stabilizing an imidazolinium quat/amine blend. The following examples disprove the expectation.

EXAMPLE 2

In this comparative example, 359.8 g of methyl di(hydrogenated tallow)amine was blended (Blend No. 59-188) in a reaction vessel with 840.2 g of methyl-1-hydrogenated tallow amide ethyl-2-hydrogenated tallow imidazolinium methyl sulfate (85.0 wt.-% in isopropanol). The imidazoline quaternary ammonium compound contained 225-285 meq/kilo (milliequivalents per kilogram) of hydrogen peroxide prior to formation of the blend. Lots of the blend were stored at various temperatures, 32.22° C. (90° F.), 43.33° (110° F.), and 54.44° C. (130° F.), and the color stability recorded at various storage time intervals.

TABLE 2

| Storage Time (weeks) | Color Stability (Hellige Color 1933) Storage Temperature (°C.) | | | Peroxide Content (Meq/Kilo) Storage Temperature (°C.) | |
|---|---|---|---|---|---|
| | 32.22 | 43.33 | 54.44 | 32.22 | 54.44 |
| Initial | 4+ | 4+ | 4+ | 225-285 | 225-285 |
| 1 | 4+ | — | 6+ | 45 | 0 |
| 2 | 4+ | 5+ | 7− | 0 | 0 |
| 3 | 4+ | 6− | 7+ | 0 | 0 |

During the second week, 0.25 wt-% $H_2O_2$ was added to a sample of Blend No. 59-188 stored at 54.44° C. No bleaching effect was observed, although the color did stabilize at 7− for the next one week of storage at 54.44° C. To another sample of Blend No. 59-188 (75 meq/kilo peroxide) which had been stored at room temperature was added to 0.7 wt-% $H_2O_2$. The color of the sample was 4+ and the peroxide content was raised to 370 meq/kilo. This sample then was placed in storage at 54.44° C. The color remained stable for one week, but the peroxide content dropped to 76 meq/kilo. Three days later the color of the product had deteriorated to 6+ and the peroxide content had dropped to less than 10.

These results demonstrate the difficulties encountered in providing an amine/imidazolinium blend which is storage stable at elevated temperature over extended periods of storage. It is quite unexpected that the same peroxide agent, which is effective in stabilizing an imidazolinium, is not effective in stabilizing the blend.

EXAMPLE 3

In this inventive example, 722 g of methyl di(hydrogenated tallow)amine was blended (Blend No. 59-196A) with 1870 g of methyl-1-hydrogenated tallow imidazolinium methyl sulfate (85.0 wt-% in isopropanol) in a reaction vessel. To this blend was added 31 g of a 33 wt-% solution of sodium bisulfite (0.1 wt-% sodium bisulfite by weight of the blend). Color stability data was recorded in the manner described in Example 2.

TABLE 3

| Storage Time (weeks) | Color Stability (Helliger Color, 1933) Storage Temperature (°C.) | | |
|---|---|---|---|
| | 32.22 | 43.33 | 54.44 |
| Initial | 5 | 5 | 5 |
| 1 | 4 | 4− | 3+ |
| 2 | 4 | 3+ | 3+ |

These results demonstrate the unexpected, yet excellent color stability which the bisulfite agent imparted to the amine/imidazolinium blend. Such color stability is seen to be obtained even at elevated storage temperatures.

EXAMPLE 4

A sample of the bisulfite-stabilized blend of Example 3 (1582 g) and isopropyl alcohol (181.5 g) were charged into a 3-liter reaction vessel and heated to 71.11° C. (160° F.). Diethyl sulfate (125.6 g) was added to the heated vessel and the contents therein maintained at 82.22°−87.70° C. (180°−190° F.) for 2 hours to make a fully quaternized amine blend (Blend No. 59-196B).

Blend 59-196B was analyzed and compared to the product specifications established for an identical quaternized amine blend (Blend No. 472) which had been prepared by simultaneously quaternizing an amine blend of methyl di(hydrogenated tallow)amine and methyl-1-hydrogenated tallow amido ethyl-2-hydrogenated tallow imidazoline.

TABLE 4

| Test | Blend No. 59-196B | Comparative Blend No. 472 |
|---|---|---|
| Appearance | Hazy Yellow Liquid at 32.22° C. | Yellow Liquid at 37.78° C. |
| Odor | Isopropanol-Fatty Type | Isopropanol-Fatty Type |
| Solids (wt-%) | 82.3 | 80-83 |
| Color (Hellinger, 1933) | 3+ | 4 max. |
| pH (5 wt-% in 1:1 isopropanol:water) | 5.8 | 5.0-7.5 |
| Ash (wt-%) | 0.32 | 0.1 max. |
| Clarity (10 wt-% in isopropanol) | Slightly hazy with trace of sediment | Trace of sediment max. |
| Free Amine (wt-%, molecular weight of 525) | 2.3 | 3.5 max. |

These results demonstrate that the precursor amine/imidazolinium blend stabilized with bisulfite can be stored at elevated temperature for extended periods of time and then fully quaternized to form a product which is in conformity with the properties of a fully quaternized product which had not been subjected to any intervening storage. It will be appreciated that the imidazoline precursor is unstable and cannot be stored unless it is quaternized. The present invention enables the mixed amine/quaternary ammonium blend to be stored, shipped, and then fully quaternized at a location where end use of the product is intended.

I claim:

1. A method for improving the storage stability at elevated storage temperatures of a blend of an amine and an imidazolinium compound which comprises adding an effective amount of an alkali metal or alkaline earth metal bisulfite agent to said blend.

2. The method of claim 1 wherein said effective amount is greater than about 0.3 weight percent.

3. The method of claim 1 wherein said effective amount ranges from between about 0.3 and 1.0 weight percent.

4. The method of claim 1 wherein said amine is present in a proportion of greater than about 5 weight percent.

5. The method of claim 4 wherein the proportion of amine ranges from between about 5 and 50 percent by weight.

6. The method of claim 1 wherein said amine is selected from the group consisting of soya dimethyl amine, hydrogenated tallow dimethyl amine, palmityl dimethyl amine, cocoa dimethyl amine, allyl dimethyl amine, benzyl dimethyl amine, dialkyl methyl amine, di(hydrogenated tallow)methyl amine, bis(2-hydroxy ethyl)cocoa amine, bis(polyhydroxy ethyl)alkyl amine, methyl alkyl benzyl amine, and mixtures thereof.

7. The method of claim 1 wherein said imidazolinium compound is selected from the group consisting of methyl-1-hydrogenated tallow amido ethyl-2-hydrogenated tallow imidazolinium methyl sulfate, methyl-1-tallow amido ethyl-2-tallow imidazolinium methyl sulfate, methyl-1-oleyl amido ethyl-2-oleyl imidazolinium methyl sulfate, 1-ethylene bis(2-tallow, 1-methyl, imidazolinium methyl sulfate), and mixtures thereof.

8. The method of claim 1 wherein said amine is methyl di(hydrogenated tallow)amine, and said imidazolinium compound is methyl-1-hydrogenated tallow amido ethyl-2-hydrogenated tallow imidazolinium methyl sulfate.

9. The method of claim 8 wherein said bisulfite agent comprises sodium bisulfite.

10. The method of claim 1 wherein said bisulfite agent comprises sodium bisulfite.

11. A storage stable blend of an amine and an imidazolinium compound which blend is stable at elevated temperatures of storage, which comprises:

(a) between about 5 and 50 percent amine;
(b) between about 95 and 50 percent imidazolinium compound; and
(c) an effective amount of an alkali metal or alkaline earth metal bisulfite agent.

12. The blend of claim 11 wherein said effective amount of said bisulfite agent ranges from between about 0.3 and 1 percent by weight.

13. The blend of claim 12 wherein said amine is methyl di(hydrogenated tallow)amine and said imidazolinium compound is methyl-1-hydrogenated tallow amido ethyl-2-hydrogenated tallow imidazolinium methyl sulfate.

14. The blend of claim 11 wherein said amine is selected from the group consisting of soya dimethyl amine, hydrogenated tallow dimethyl amine, palmityl dimethyl amine, cocoa dimethyl amine, allyl dimethyl amine, benzyl dimethyl amine, dialkyl methyl amine, di(hydrogenated tallow)methyl amine, bis(2-hydroxy ethyl)cocoa amine, bis(polyhydroxy ethyl)alkyl amine, methyl alkyl benzyl amine, and mixtures thereof.

15. The blend of claim 11 wherein said imidazolinium compound is selected from the group consisting of methyl-1-hydrogenated tallow amido ethyl-2-hydrogenated tallow imidazolinium methyl sulfate, methyl-1-tallow amido ethyl-2-tallow imidazolinium methyl sulfate, methyl-1-oleyl amido ethyl-2-oleyl imidazolinium methyl sulfate, 1-ethylene bis(2-tallow, 1-methyl, imidazolinium methyl sulfate), and mixtures thereof.

* * * * *